United States Patent [19]

Hermecz et al.

[11] Patent Number: 4,940,794

[45] Date of Patent: Jul. 10, 1990

[54] QUINOLINE CARBOXYLIC ACID BORIC ACID ANHYDRIDES

[75] Inventors: István Hermecz; Géza Kereszturi; Lelle Vasvári; Ágnes Horvath, all of Budapest; Mária Halogh, Dunakeszi; Péter Ritli, Budapest; Judit Sipos, Budapest; Anikó Pajor, Budapest; Katalin Mármarosi, Bidatórbágy, all of Hungary

[73] Assignee: Chinoin Gyogyszer es Vegyeszeti Termekek Gyara/Rt., Budapest, Hungary

[21] Appl. No.: 290,167

[22] PCT Filed: Apr. 8, 1988

[86] PCT No.: PCT/HU88/00018

§ 371 Date: Dec. 2, 1988

§ 102(e) Date: Dec. 2, 1988

[87] PCT Pub. No.: WO88/07998

PCT Pub. Date: Oct. 20, 1988

[30] Foreign Application Priority Data

Apr. 8, 1987 [HU] Hungary ............................... 1504/87
Jun. 24, 1987 [HU] Hungary ............................... 2857/87
Jul. 10, 1987 [HU] Hungary ............................... 3147/87

[51] Int. Cl.$^5$ ................................................ C07F 5/02
[52] U.S. Cl. ...................................................... 546/13
[58] Field of Search ............................................ 546/13

[56] References Cited

U.S. PATENT DOCUMENTS 4,803,274 2/1989 Hermecz et al. ....................... 546/13
4,806,645 2/1989 Hermecz et al. ....................... 546/13

FOREIGN PATENT DOCUMENTS 62-294689 12/1987 Japan ..................................... 546/13
WO87/03586 6/1987 PCT Int'l Appl. .................... 846/13
87/03587 6/1987 PCT Int'l Appl. .................... 546/13

Primary Examiner—Robert T. Bond
Attorney, Agent, or Firm—Herbert Dubno; Jonathan Myers

[57] ABSTRACT

The invention relates to new quinoline-3-carboxylic acid anhydride intermediates of the Formula I

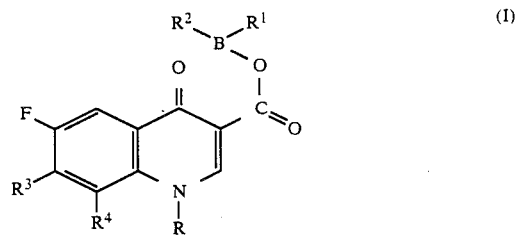

wherein R stands for cyclopropyl, a group of the Formula —CH$_2$CR$^5$R$^6$R$^7$ wherein R$^5$, R$^6$ and R$^7$ stand for hydrogen or halogen, or phenyl optionally substituted by 1 or 2 halogen, R$^1$ and R$^2$ stand for halogen, or an aliphatic acyloxy group containing 2 to 6 carbon atoms optionally substituted by halogen, or an aromatic acyloxy group containing 7 to 11 carbon atoms, R$^3$ stands for chlorine or fluorine and R$^4$ stands for hydrogen or fluorine. The compounds of the Formula I are new intermediates for the preparation of known quinoline-3-carbocxylic acids showing antibacterial activity.

2 Claims, No Drawings

QUINOLINE CARBOXYLIC ACID BORIC ACID ANHYDRIDES

CROSS REFERENCE TO RELATED APPLICATIONS

This application is a national phase application of PCT/HU88/00018 filed 8 Apr. 1988 and based in turn, on Hungarian national applications 1504/87 filed 8 Apr. 1987, 2857/87 filed 24 Jun. 1987 and 3747/87 filed 10 Jul. 1987, under the International Convention.

This invention relates to new 1-substituted-6-fluoro-7-substituted-8-optionally fluoro-substituted-4-oxo-1,4-dihydro-quinoline-3-carboxylic-acid-boric acid-anhydride derivatives of the Formula I

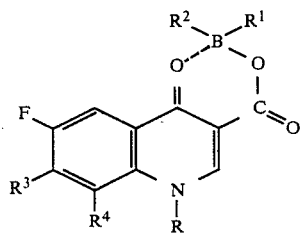

and to a process for the preparation thereof.

In the general Formula I

R stands for cyclopropyl, or a group of the general Formula —$CH_2CR^5R^6R^7$ (wherein $R^5$, $R^6$ and $R^7$ stand for hydrogen or halogen) or phenyl optionally substituted by 1 or 2 halogen atoms, $R^1$ and $R^2$ are the same or different and stand for halogen, or an aliphatic acyloxy group containing 2 to 6 carbon atoms being optionally substituted by halogen, or an aromatic acyloxy group containing 7 to 11 carbon atoms, $R^3$ stands for chlorine or fluorine and $R^4$ stands for hydrogen or fluorine.

BACKGROUND OF THE INVENTION

Ethyl(1-p-fluorophenyl-6-fluoro-7-chloro-4-oxo-1,4-dihydro-quinoline-3-carboxylate) is an intermediate for the preparation of 1-p-fluorophenyl-6-fluoro-1,4-dihydro-4-oxo-7-(4-methyl-1-piperazinyl)-3-quinoline-carboxylic acid of antibacterial activity (24th Intersci. Conf. Antimicrob. Agents. Chemother. 1984. Abst. 72-78). The latter compound can be prepared from ethyl-(1-p-fluorophenyl-6-fluor-7-chloro-4-oxo-1,4-dihydro-quinoline-3-carboxylate) in two steps. The 1-p-fluorophenyl-6-fluoro-1,4-dihydro-4-oxo-7-(4-methyl-1-piperazinyl)-3-quinoline-carboxylic acid can be prepared by reacting 1-p-fluorophenyl-6-fluoro-7-chloro-1,4-dihydro-4-oxo-quinoline-3-carboxylic acid (obtained by hydrolyzing the ester) with 1-methyl-piperazine in the presence of a solvent at a temperature of 100° C. for 20 hours (European Patent Specification No. 131839).

The ethyl-(1-cyclopropyl-6-fluoro-7-chloro-4-oxo-1,4-dihydro-quinoline-3-carboxylate) is an intermediate for the preparation of 1-cyclopropyl-6-fluoro-1,4-dihydro-4-oxo-7-(1-piperazinyl)-3-quinoline-carboxylic acid which has antibacterial activity (Eur. J. Clin. Microbiol. 1983., 2, 111). The latter compound can be obtained from ethyl-(1-cyclopropyl-6-fluoro-7-chloro-4-oxo-1,4-dihydro-quinoline-3-carboxylate) in two steps. After hydrolyzing the ester, the 1-cyclopropyl-6-fluoro-7-chloro-1,4-dihydro-4-oxo-quinoline-3-carboxylic acid thus obtained is reacted with piperazine in the presence of a solvent at a temperature of 135°-140° C. for two hours and thus 1-cyclopropyl-6-fluoro-1,4-dihydro-4-oxo-7(1-piperazinyl)-quinoline-3-carboxylic acid can be prepared (German Off. No. 30 33 157 and No. 31 42 854).

The 1-substituted-6,7,8-trifluoro-4-oxo-1,4-dihydro-quinoline-3-carboxylic acid derivatives (GB patent No. 2057440, Belgian patent specification 887574, European patent No. 106489 and No. 15049, German patent No. 3433924, Japanese patent Nos. 60006684 and 61085381, Portugal patent No. 80187) are intermediates for the preparation of 7-substituted-6,8-difluoro-1,4-dihydro-4-oxo-quinoline-3-carboxylic acid derivatives (J. Med. Chem. 1986. 29, 445; Drugs Fut. 1984. 9, 246; 23rd Intersci. Conf. Antimicrob. Agents Chemother. 1983. Abstr. 658; 7th Int. Symp. Fut. Trends Chemother. 1986, 80).

DESCRIPTION OF THE INVENTION

According to the present invention 1-(optionally halo-substituted)ethyl-6,8-difluoro-1,4-dihydro-4-oxo-7-substituted-quinoline-3-carboxylic acid derivatives, 1-cyclopropyl-6-fluoro-1,4-dihydro-4-oxo-7-(optionally substituted piperazino)-quinoline-3-carboxylic acid derivatives and 1-substituted-6-fluoro-1,4-dihydro-4-oxo-7(optionally substituted piperazino)-quinoline-3-carboxylic acid derivatives can be prepared in a simple manner by applying the new compounds of the general Formula I as starting material.

The compounds of the Formula I (wherein R, $R^1$, $R^2$, $R^3$ and $R^4$ are the same as stated above) can be obtained by reacting a compound of the Formula

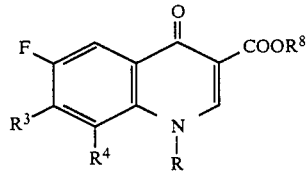

wherein $R^8$ stands for hydrogen or alkyl containing 1 to 4 carbon atoms and fluoroborate of the Formula III

or a boron trihalide of the Formula IV

wherein X stands for fluorine, chlorine or bromine, or an ether complex thereof or a triacyloxy borate derivative of the Formula V

wherein $R^9$ stands for alkyl containing 1 to 5 carbon atoms optionally substituted by halogen or aryl containing 6 to 10 carbon atoms.

Borone trifluoride, boron tribromide, boron trichloride and complexes or aqueous solutions of these compounds can be used as compounds of the Formula IV. Preferably complexes of ethers or alcohols may be used (e.g. a complex of boron trifluoride with tetrahydrofuran, diethyl ether, methanol or propanol). If desired the solutions of boron trihalide and aliphatic hydrocarbons (e.g. hexane) or halohydrocarbons (e.g. dichloromethane) or carboxylic acids (e.g. acetic acid, trifluoro acetic acid, propionic acid) may be used.

The fluoroborate of the Formula III, the boron-trihalides and its complexes of the Formula IV and the triacyloxy borate derivatives of the Formula V can be used in a molar ratio of 50:1, preferably 5:1 related to the compounds of the Formula II. However, if desired, other molar ratios may also be used.

The reaction may also be carried out in the presence of a solvent. As solvent one may use water, ketones (e.g. acetone, methyl ethyl ketone), hydrocarbons (e.g. hexane, benzene, toluene), ethers (e.g. diethyl ether, dioxane, tetrahydrofuran) or organic acids (e.g. acetic acid, propionic acid, trifluoroacetic acid).

If desired the reagents can be reacted at room temperature. If the reaction is carried out at higher temperature, the reaction time can be shortened. One may preferably carry out the reactions at a temperature ranging from 20° to 150° C., but the reaction temperature depends on the solvent applied.

The compounds of the Formula I precipitate from the reaction mixture spontaneously or on cooling and thus can be separated e.g. by filtration.

Further details of the present invention are to be found in the following Examples without limiting the scope of protection to said Examples.

EXAMPLE 1

4.6 g of acetic acid are added to the mixture of 0.93 g of boric acid and 1.5 mg of zinc chloride whereupon the suspension is heated slowly under stirring. A clear solution is obtained at 80° C. A solution of 3.1 g of ethyl-(1-cyclopropyl-6-fluoro-7-chloro-1,4-dihydro-4-oxo-quinoline-3-carboxylate) with 5 ml of hot 96 w/v % acetic acid is added dropwise to the clear solution at 100° C. The reaction mixture is stirred at 110° C. for two hours, then cooled to 10° C. and diluted with 10 ml of water. The suspension thus obtained is stirred at 10° C. for two hours. The precipitated cream-coloured crystals are filtered, washed with water and ethanol and dried. Thus 4.02 g of (1-cyclopropyl-6-fluoro-7-chloro-1,4-dihydro-4-oxo-quinoline-3-carboxylate-$O^3,O^4$)bis-(acetato-O)-boron are obtained. The product decomposes at 254°–256° C.

| Analysis for the Formula $C_{17}H_{14}O_7NBClF$: | | | |
|---|---|---|---|
| Calculated: | C = 49.86% | H = 3.45% | N = 3.42% |
| Found: | C = 50.03 | H = 3.41% | N = 3.50%. |

EXAMPLE 2

3.0 g of ethyl-(1-ethyl-6,7,8-trifluoro-1,4-dihydro-4-oxo-quinoline-3-carboxylate) are stirred in 15 ml of 50 w/v % aqueous hydrogen-tetrafluoro-borate solution at 80°–90° C. for 2.5 hours. The precipitation of the crystals from the clear solution begins after half an hour whereupon a thick suspension is obtained. The reaction mixture is cooled to room temperature and crystallized overnight by cooling on ice. The precipitated crystals are filtered and washed with water and methanol. After drying 3.1 g of (1-ethyl-6,7,8-trifluoro-1,4-dihydro-4-oxo-quinoline-3-carboxylate-$O^3,O^4$)-difluoro-boron are obtained. The product decomposes at 289° C.

| Analysis for the Formula $C_{12}H_7BF_5NO_3$: | | | |
|---|---|---|---|
| Calculated: | C = 45.18% | H = 2.21% | N = 4.40% |
| Found: | C = 45.26% | H = 2.18% | N = 4.32%. |

EXAMPLE 3

A mixture of 0.93 g of boric acid and 6.9 g of propionic acid anhydride is stirred at 95°–100° C. for 30 minutes. A solution of 3.0 g of ethyl(1-ethyl-6,7,8-trifluoro-1,4-dihydro-4-oxo-quinoline-3-carboxylate) in 12 ml of warm propionic acid is added to the reaction mixture under steady heating. The red solution thus obtained is stirred at 110° C. for 5 hours and then cooled to room temperature and diluted with 150 ml of water. The precipitated crystals are filtered, washed with water and methanol and dried. Thus 4.1 g of (1-ethyl-6,7,8-trifluoro-1,4-dihydro-4-oxo-quinoline-3-carboxylate-$O^3,O^4$)-bis(propionato-O)-borone are obtained. The product decomposes at 195°–196° C.

| Analysis for the Formula $C_{18}H_{17}BF_3NO_7$: | | | |
|---|---|---|---|
| Calculated: | C = 50.61% | H = 4.01% | N = 3.29% |
| Found: | C = 50.72% | H = 4.11% | N = 3.31%. |

EXAMPLE 4

10 ml of acetic acid anhydride are added to the mixture of 1.85 g of boric acid and 20 mg of zinc chloride. The suspension is stirred while the temperature of the mixture rises to 80° C. and then decreases. Stirring is continued for a further hour at 110° C., whereupon a solution of 6.0 g of ethyl-(1-ethyl-6,7,8-trifluoro-1,4-dihydro-4-oxo-quinoline-3-carboxylate) in 20 ml of warm 96 w/v % acetic acid is added dropwise. The reaction mixture is stirred at 110° C. for two hours and cooled to room temperature. 150 ml of water are added to the reaction mixture and the suspension thus obtained is stirred under cooling for 3 hours. The precipitated crystals are filtered, washed with water and methanol and dried. Thus 7.7 g of (1-ethyl-6,7,8-trifluoro-1,4-dihydro-4-oxo-quinoline-3-carboxylate-$O^3,O^4$)bis-(acetato-O)-boron are obtained. The product decomposes at 211° C.

| Analysis for the Formula $C_{16}H_{13}BF_3NO_7$: | | | |
|---|---|---|---|
| Calculated: | C = 48.15% | H = 3.28% | N = 3.52% |
| Found: | C = 48.12% | H = 3.28% | N = 3.54%. |

EXAMPLE 5

3.64 g (0.01 mole) of 1-(4'-fluoro-phenyl)-6-fluoro-7-chloro-1,4-dihydro-4-oxo-quinoline-3-carboxylic acid ethyl ester are added to 30 ml of 50 w/v % aqueous hydrogen tetrafluoro borate(III) solution under stirring whereupon the reaction mixture is heated to 110° C. The solution thus obtained is stirred at 110° C. for two hours while the precipitation begins. The reaction mixture is cooled and crystallized overnight by cooling with ice. The precipitated crystals are filtered, washed with 5 ml of water and 5 ml of methanol. Thus 3.66 g of [1-(4'-fluoro-phenyl)-6-fluoro-7-chloro-1,4-dihydro-4-oxo-quinoline-3-carboxylate-$O^3,O^4$]-difluoro-boron are obtained as white crystals. M.p.: 324°–326° C.

| Analysis for the Formula $C_{16}H_7NO_3BF_4Cl$: | | |
|---|---|---|
| Calculated: C = 50.11% | H = 1.84% | N = 3.65% |
| Found: C = 50.21% | H = 1.92% | N = 3.68%. |

EXAMPLE 6

4.59 g of acetic acid are added to the mixture of 0.93 g of boric acid and 1.5 mg of zinc chloride whereupon the suspension is heated slowly under stirring. A clear solution is obtained at 80° C. A solution of 3.64 g (0.01 mole) of 1-(4'-fluoro-phenyl)-6-fluoro-7-chloro-1,4-dihydro-4-oxo-quinoline-3-carboxylic acid ethyl ester in 20 ml of hot 96 w/v % acetic acid is added dropwise to the clear solution at 100° C. The reaction mixture is stirred at 110° C. for 3 hours, cooled and diluted with 10 ml water. The mixture is crystallized overnight by cooling with ice. The precipitated white crystals are filtered, washed with 5 ml of water and 5 ml of ethanol. Thus 4.54 g of crystalline [1-(4'-fluoro-phenyl)-6-fluoro-7-chloro-1,4-dihydro-4-oxo-quinoline-3-carboxylate-$O^3,O^4$]bis(acetato-O)-boron are obtained. The product decomposes at 248°–250° C.

| Analysis for the Formula $C_{20}H_{13}NO_7BF_2Cl$: | | |
|---|---|---|
| Calculated: C = 51.82% | H = 2.83% | N = 3.02% |
| Found: C = 52.01% | H = 2.91% | N = 3.07%. |

EXAMPLE 7

5.3 g of 97 w/v % propionic acid anhydride are added to the mixture of 0.93 g of boric acid and 1.5 mg of zinc chloride whereupon the suspension is heated slowly under stirring. A clear solution is obtained at 90° C. 3.64 g (0.01 mole) of 1-(4'-fluoro-phenyl)-6-fluoro-7-chloro-1,4-dihydro-4-oxo-quinoline-3-carboxylic acid ethyl ester are added to the solution and the reaction mixture is stirred at 110° C. for half an hour then cooled and diluted with 6 ml of water. The mixture is crystallized overnight by cooling with ice. The precipitated crystals are filtered and washed with 5 ml of water and 5 ml of ethanol. Thus 4.72 g of crystalline [1-(4'-fluoro-phenyl)-6-fluoro-7-chloro-1,4-dihydro-4-oxo-quinoline-3-carboxalate-$O^3,O^4$]-dipropionato-boron are obtained. The product decomposes at 278°–280° C.

| Analysis for the Formula $C_{22}H_{17}NO_7BF_2Cl$: | | |
|---|---|---|
| Calculated: C = 53.75% | H = 3.49% | N = 2.85% |
| Found: C = 53.71% | H = 3.39% | N = 2.79%. |

What we claim is:
1. A compound of the Formula (I)

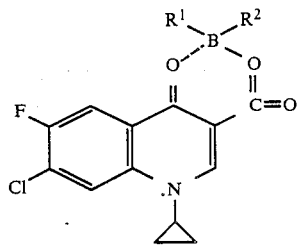

wherein
$R^1$ and $R^2$ are each halogen, or an aliphatic acyloxy group containing 1 to 4 carbon atoms optionally substituted by halogen, or an aromatic acyloxy group containing 7 to 11 carbon atoms.
2. (1-cyclopropyl-6-fluoro-7-chloro-1,4-dihydro-4-oxo-quinoline-3-carboxylate-$O^3,O^4$)bis(acetato-O)-boron as defined in claim 1.

* * * * *